United States Patent [19]

Kanno

[11] Patent Number: 4,661,059
[45] Date of Patent: Apr. 28, 1987

[54] ORTHODONTIC BRACKET AND APPARATUS FOR FABRICATING THE SAME

[76] Inventor: Yoneo Kanno, 5-181-96, Higashi Hatsuishi Nagareyama, Chiba, Japan

[21] Appl. No.: 651,746

[22] Filed: Sep. 18, 1984

[30] Foreign Application Priority Data

Sep. 22, 1983 [JP] Japan ................................ 58-174183

[51] Int. Cl.⁴ .............................................. A61C 3/00
[52] U.S. Cl. ...................................................... 433/9
[58] Field of Search ..................... 433/9, 8, 10, 11, 12, 433/13, 14, 15, 16, 17

[56] References Cited

U.S. PATENT DOCUMENTS 4,322,206 3/1982 Reynolds ................................ 433/9
4,430,061 2/1984 Webb et al. .............................. 433/9

Primary Examiner—John J. Wilson
Attorney, Agent, or Firm—Rhodes and Boller

[57] ABSTRACT

An orthodontic bracket with reinforced retentive forces is provided by forming, in the undersurface of the bracket, a plurality of fine grooves in one direction and a plurality of fine grooves in the other direction crossing the first-mentioned direction. These fine grooves are formed by a cutting machine having a plurality of rotatable thin circular cutter blades. The grooves are of relatively deep square or rectangular cross section and capable of firmly retain relatively large quantity of adhesives. The bracket of the invention, when bonded to the tooth surface by the use of adhesives, is not subject to separation of adhesives from the metal surface.

5 Claims, 13 Drawing Figures

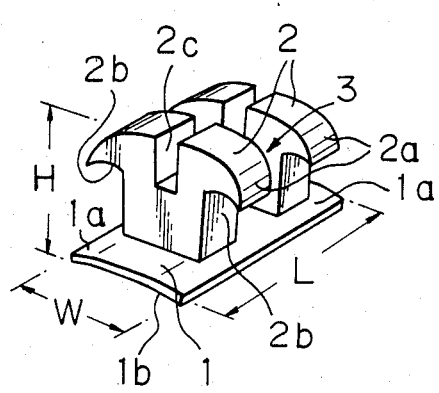
Fig. 1
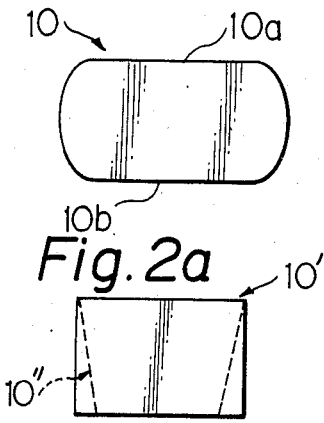
Fig. 2
Fig. 2a
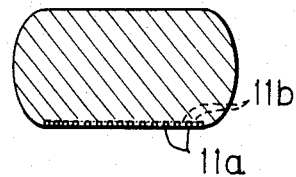
Fig. 3
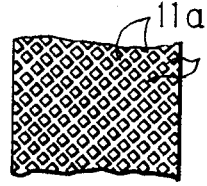
Fig. 4A
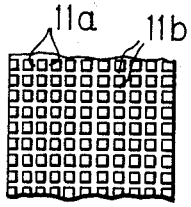
Fig. 4B
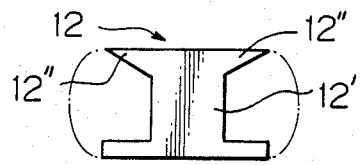
Fig. 5
Fig. 6
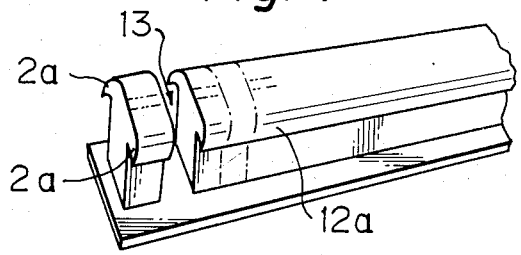
Fig. 7

ORTHODONTIC BRACKET AND APPARATUS FOR FABRICATING THE SAME

BACKGROUND OF THE INVENTION

This invention relates generally to brackets for use in orthodontics and more particularly to brackets with high retentive forces and an apparatus for fabricating such brackets.

An orthodontic bracket is one of appliances to be used in orthodontics, i.e. for reforming an irregular set of teeth. In orthodontic operations, brackets are fixed by adhesives to adjacent teeth and bound together by connecting wires or thin rods to impose a corrective force upon a particular tooth to be reformed.

In general, the orthodontic bracket is composed of two parts, i.e. a main body to which wires or rods are engaged, and a welding flange or base from which the main body is projecting and which is to be welded or bonded to the tooth surface. Heretofore, the main body was welded or otherwise secured to the base to make up the orthodontic bracket.

Such combined brackets, however, have many defects and disadvantages, such as (I) separation of the main body from the base due to heavy stresses imposed by fastened wires;

(II) difficulties and inaccuracy in bonding the main body onto the base; and (III) peeling off from the base of a net member, which is fixed to the undersurface of the base in order to reinforce retentive forces between the teeth and the brackets.

In view of these circumstances, I have provided a method for fabricating a bracket in which a main body and a base plate are originally and essentially integral with each other by cutting and bending operations of a unitary and continuous rod material into a shape of integral main body and base plate (Japanese patent application No. 174157/1982).

In the above-mentioned method, the undersurface of the base is preferably formed with rough surfaces so as to strengthen the retentive forces of the adhesives against the undersurface of the base. By such method, however, the retentive forces between the base and the adhesive has not been found sufficiently strong.

OBJECTS OF THE INVENTION

It is, therefore, an object of the present invention to provide an orthodontic bracket with high retentive forces in which a main body and a base plate are originally of integral structure and in which the base has formed on its undersurface with a first row of fine and deep grooves and a second row of fine and deep grooves crossing the first row of grooves so as to assure high and strong retentive forces.

It is another object of the invention to provide an apparatus for fabricating such brackets by cutting easily and securely the crossing fine grooves in the undersurface of the base member of the bracket.

SUMMARY OF THE INVENTION

The present invention provides an orthodontic bracket in which a main body and a base plate are originally continuous and integral with each other and the base plate is provided in its undersurface with different rows of fine grooves crossing each other and retaining firmly much more adhesives than those heretofore available. Each groove is of square cross section and far more deeper than the conventional means such as punched holes or meshes of a net attached to the undersurface of the bracket, so that the groove of the invention can accommodate much more adhesive than the conventional means and the bracket of the invention can be retained firmly and securely onto the tooth surface.

In addition, the grooves fabricated according to the invention can have small protrusions or so called "fins" or "flashes" at the edges of the grooves resulting from cutting operations of cutter blades scraping metal matrix at high speed. These small protrusions may be pressed down into the inside of the groove edges to form mechanical retentive means for adhesives received in the grooves.

The fine crossing grooves are worked by a cutting machine of the invention which includes a novel cutter assembly comprising a plurality of saw-toothed circular cutter blades assembled on a common rotating shaft or arbor with thin space therebetween. The cutting machine also includes workpiece holders which are adapted to be mounted with a desired or varied angular disposition with respect to the rotatable cutter assembly. By using workpiece holders of different angular disposition, different rows of fine grooves crossing each other can be easily formed at a stroke.

BRIEF DESCRIPTION OF THE DRAWINGS

FIG. 1 is an enlarged perspective view of an exemplary orthodontic bracket according to the present invention;

FIG. 2 through FIG. 7 illustrate the consecutive steps for fabricating an integral-structure bracket according to the invention, FIG. 2 showing an end view of a stock material having rod-like shape of relatively flat sectional configuration, FIG. 2a showing another example of a stock material, FIG. 3 being a sectional view of the stock material provided in its undersurface with fine crossing grooves, FIGS. 4A and 4B illustrating respectively examples of crossing fine grooves, FIG. 5 showing an end view of semi-processed material having an "I-beam" cross section resulting from cutting out lateral portions, FIG. 6 showing the semi-processed material subjected to bending operation on its longitudinal ribs, FIG. 7 being a perspective view showing a fabricating step to cut main bodies out of longitudinally continuous semi-processed material shown in FIG. 6.

DETAILED DESCRIPTION OF THE EMBODIMENTS

Figure 8:
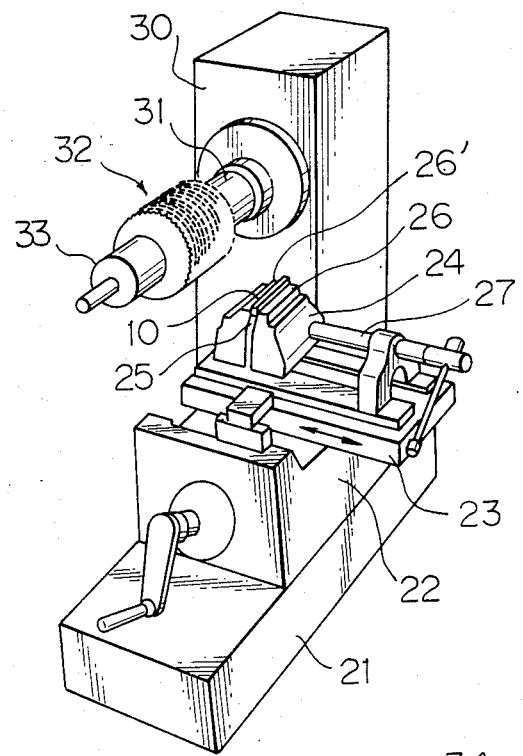
FIG. 8 illustrates an embodiment of the apparatus of the invention for cutting the crossing fine grooves in the undersurface of the stock material as shown in FIG. 3.

Referring now to the drawings, the invention will be described in detail in connection with an orthodontic bracket itself shown in FIGS. 1 through 7 and an apparatus for fabricating the same shown in FIGS. 8 and 9.

In FIG. 1, an orthodontic bracket is shown which comprises a base plate 1 and two main bodies 2 originally integral with the base 1. Single main body or three or more main bodies may be employed in accordance with specific applications. Usually, the bracket may be made of stainless steel.

Side edges 1a of the base 1 are slightly bent toward the undersurface 1b to accommodate themselves to the contour of the tooth surface. The undersurface 1b of the base 1 is to be bonded to the tooth surface by means of an appropriate adhesive. For this purpose, the undersurface 1b is provided with fine crossing grooves as illustrated in FIGS. 4a or 4b by cutting operations of an apparatus shown in FIG. 8. These crossing fine grooves serve to attain far more strong retentive forces between the metal surface of the bracket and the adhesives.

The main body 2 of the bracket has at its each side a bent arm 2a below which a pocket 2b is formed to accommodate used to tie up several brackets attached to several teeth. A recessed portion 2c is formed at the top of the main body 2 to accommodate a thin rod member connecting several brackets.

Two main bodies 2 as shown in FIG. 1 are spaced apart from each other by a notched portion 3 reaching the upper surface of the base plate 1.

As an example, the bracket shown in FIG. 1 has a height H of about 1.6 to 2.0 mm, a width W of about 3 mm and a length L of about 4 mm.

Referring now to FIG. 2 through FIG. 7, a fabricating process of the bracket of the invention will be described.

A first step of the process includes rolling stainless steel rods of circular cross section into a rod-like stock material 10 of relatively flat cross section as shown in FIG. 2. Stock material 10 has a top surface 10a and a bottom surface 10b which are substantially straight and parallel to each other. Stock material 10 has opposite lateral surfaces convexly protruding which are to be removed later during milling operation.

Alternatively, the stock material may be prepared as illustrated in FIG. 2a in which stock material 10' having substantially rectangular cross section of about 3mm width and 2 mm thick can be obtained by slitting sheet metals. Stock material of trapezoidal cross section or of inverse trapezoided cross section 10" as shown in FIG. 2 can also be employed. Stock material 10" of inverse trapezoidal shape is particularly suitable in fabricating a bracket having a small area base plate, which bracket is advantageously recommended because, when applied to the tooth surface, it will leave larger free area on the tooth surface to be easily cleaned as by a tooth-brush to avoid decayed teeth.

Next step is, as shown in FIGS. 3, 4A and 4B, to form crossing fine grooves 11a and 11b in the undersurface of the rolled or flattened stock material 10, 10' or 10". These grooves 11a and 11b are formed by a cutting machine as shown in FIG. 8. The grooves 11a and 11b are of square or rectangular cross section and have much more volume to accommodate adhesives than the retention means heretofore employed, such as net members bonded or welded to the undersurface of the base or minute holes made by punching operations in the undersurface of the base. Further, the grooves 11a and 11b are far more reliable in retaining the bracket on the tooth surface than the net member because they won't peel out like the bonded net member.

A preferred arrangement of the crossing grooves is shown in FIG. 4A in which a first row 11a of the grooves and a second row 11b of the grooves are crossing each other and both are diagonally arranged with respect to the longitudinal axis of the stock 10. Also preferred is an arrangement shown in FIG. 4B in which a first row 11a is parallel to the longitudinal axis and a second row 11b is transverse to the first row. In any event, as much volume to accommodate adhesives as possible is desired to be made on the undersurface of the stock material.

Figure 9:
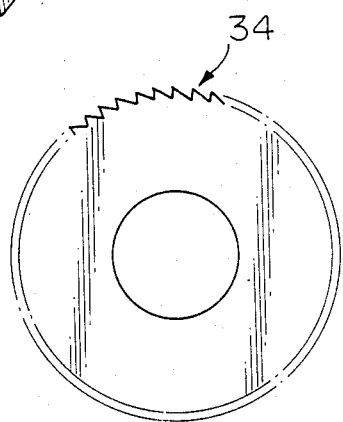
FIG. 9 shows diagrammatically an example of a cutter blade employed in the apparatus of FIG. 8, FIGS. 10 and 11 are views showing more detail.
Figure 10:
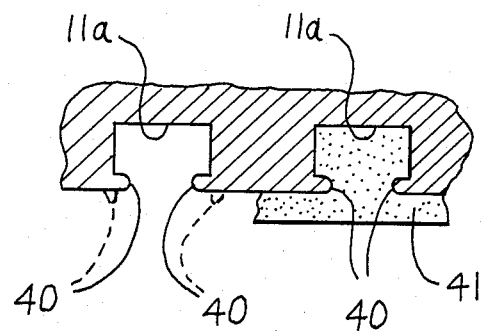

In cutting the grooves by the cutting machine shown in FIG. 8, fins, flashes or small protrusions 40 (see FIG. 10) are inevitably formed on the edge portions of the grooves adjacent to the under surface of the stock metal. In accordance with the present invention, these protrusions are advantageously utilized to develop mechanical retentive force for adhesives 41 accommodated in the grooves 11a and 11b. That is, after forming the grooves, these protrusions or fins 40 are pressed down from the broken line position to the solid line position by applying pressure onto the undersurface thereby to deform and bend the protrusions into the grooves. Protrusions thus deformed will close partially openings of the grooves adjacent to its edges and will bite into adhesives applied into the grooves and over the undersurface of the stock material.

Figure 11:
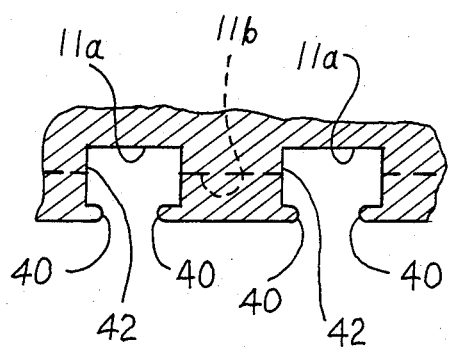

Small fins or flashes 42 can also be made at crossing points of two grooves if two crossing grooves are formed in different depths. (See Fig. 11) Where deeper grooves 11a are formed first and shallower grooves crossing the deeper grooves are cut next, fins or flashes are developed substantially horizontally at the bottom edges of shallower grooves partially projecting over the deeper grooves. These horizontal projections function as mechanical retentive means for adhesives in the deeper grooves as they are.

The stock material 10 thus formed with crossing fine grooves at its bottom surface are then subjected to a third step wherein opposite lateral portions of the stock are removed by milling work to provide a semi-processed material 12 having a cross section like an "I-beam" as shown in FIG. 5. Dot and dash lines in FIG. 5 indicate portions removed from the stock 10. Milling operation is conducted so as to shape a trunk portion 12' having at its top laterally projecting convergent ribs 12" and at its base laterally projecting thin plates of about 0.3 mm thick which will form a base plate 1 as shown in FIG. 1. In FIG. 5, the ribs and the plates are shown as having the substantially same width. However, if a semi-processed material 12 is worked from the inverse trapezoidal stock 10" of FIG. 2A, then the ribs 12" will be of greater width than the plates. Because of recently developed strong adhesives for use in orthodontics, even smaller base plate can have sufficiently strong retentive forces and be advantageously employed by the reasons as mentioned above.

The semi-processed material 12 thus obtained is then subjected to a fourth step wherein each rib 12" is bent toward the base as by press working to form bent rib 12a. The bent ribs 12a are extending longitudinally along each side of the trunk 12' and will be bent arms 2a of FIG. 1 when subjected to milling work (a fifth step).

FIG. 7 illustrates a fifth step wherein the semi-processed material with bent ribs 12a undergoes milling operation transversely to the longitudinal axis at predetermined distance to form notched portion 13 between the members which will be the main bodies 2 after a seventh step. Milling operations may be performed transversely to the longitudinal axis as indicated by a dot-and-dash line in FIG. 7 though it may also be performed angularly to the longitudinal axis, if desired, to produce so called "angular type" brackets. The depth of notched portions 13 may reach the surface of the base plate 1 or may terminate at midway as may be required by a specifically intended use. By milling operations, bent ribs 12a are changed into bent arms 2a.

Then, a sixth step is conducted as shown by two-dots-and-dash lines in FIG. 7 to remove top center portions by milling in order to form recessed portions 2c as shown in FIG. 1. Recessed portions may be made angularly to the vertical, if necessary, or according to specific requirements.

Thus, several candidate main bodies 2 are formed on the continuous single base plate which, in seventh step, is to be sliced off at a predetermined distance to produce semi-finished bracket having desired number of main bodies. Slicing at every two main bodies will produce the bracket as shown in FIG. 1. Slicing may be made with the same angle as or different angle from that of milling to form notched portions 13.

Finally, an eighth step is to slightly bend lateral edges of the base plate to form the finished product with slightly curved edges 1a.

Turning now to FIG. 8, a cutting machine of the invention to be used with the aforementioned second step is described. The machine includes a base 21 on which is mounted a guide block 22 which, in turn, supports on its upper surface a feeder 23. Feeder 23, which is adapted to be moved back and forth as indicated by arrows, supports detachably and replaceably a workpiece holder 24 which has two holding edges 26 and 26' spaced apart by a slot 25. In the slot 25, the above-mentioned stock material 10, 10' or 10" is securely held to undergo groove-forming cutting operations. After the material 10, 10' or 10" is inserted in the slot 25, an adjusting screw 27 is rotated to fasten and lock the holding edges 26 and 26'.

An upright housing 30 contains a driving mechanism from which extends an arbor 31 having thereon a cutter assembly 32. The cutter assembly 32 comprises a plurality of circular cutting blades 34. An individual blade 34 is diagrammatically shown in FIG. 9 and has saw teeth on its circular edge. Such cutting blades 34 are assembled on the arbor 31 with thin space therebetween to compose the cutter assembly 32 rotating with the arbor 31. The individual blade 34, when rotated, is intended to cut an individual groove. The cutting assembly 32 is held on the arbor 31 by a retainer 33.

Though the workpiece holder 24 shown in FIG. 8 is disposed in such a position as to cut fine grooves transverse to the longitudinal axis of the material 10 (the grooves 11b shown in FIG. 4B), another workpiece holders may be replaceably mounted on the feeder 23 in another positions to make parallel (as 11a of FIG. 4B) or inclined (as 11a and 11b of FIG. 4A) grooved.

Thus, in accordance with the invention, the fine grooves can be formed in a desired angular disposition by using an appropriate holder 24 capable of holding the stock material 10 in the desired angular disposition with respect to the assembled cutter blades 34. By using two holders of different angular dispositions, different rows of fine grooves crossing each other can be obtained at a stroke in far more density and depth than those heretofore obtained by any conventional means. In addition to the greater volume accommodating more adhesives, the grooves made by the invention can be provided with mechanical retention means biting into adhesives at the edges of grooves or crossing points of two grooves and, thus, much far strong retentive forces can be attained between the orthodontic bracket and the tooth surface.

The brackets of the present invention have many advantages and effects in that there is no possibility of any fracture or peeling out as they are of originally and essentially integral structure, that they can firmly retain more adhesives in a large number of crossing fine grooves and exhibit strong retentive forces on the tooth surface so that prescribed orthodontic effects are assured without fail, and that they can be produced by relatively simple machining operations and be supplied at lower costs.

I claim:

1. Orthodontic bracket with reinforced retentive forces comprising: a base plate (1) and at least one main body (2) standing thereon, both base plate and main body being worked up from originally unitary stock material (10), said main body having at its top a recessed portion (2c) and at its each side a bent arm (2a), said base plate having at its undersurface a plurality of fine crossing grooves (11a, 11b) formed by cutting work, said grooves having along their edges small protrusions formed during cutting and subsequently deformed into the grooves so as to close partially the openings of the grooves, said deformed protrusions exhibiting mechanical retentive forces against adhesives received and solidified in the grooves.

2. Orthodontic bracket as claimed in claim 1 wherein said fine crossing grooves comprises a first row of grooves and a second row of grooves crossing said first row of grooves.

3. Orthodontic bracket as claimed in claim 2 wherein in said first row of grooves are arranged transversely to the longitudinal axis of the bracket and said second row of grooves are arranged parallel to said axis.

4. Orthodontic bracket as claimed in claim 2 wherein said first row of grooves are obliquely arranged with respect to the longitudinal axis of the bracket and said second row of grooves are also obliquely to said axis and crossing said first row of grooves.

5. Orthodontic bracket as claiimed in claim 2 wherein said first and second rows of grooves are formed respectively in different depths, and small fins are formed at the crossing points of the two grooves and projecting in the deeper grooves.

* * * * *